(12) United States Patent
Aharoni et al.

(10) Patent No.: US 12,109,106 B1
(45) Date of Patent: Oct. 8, 2024

(54) SULCUS FIXATION FRAME

(71) Applicant: Samsara Vision Ltd., Petah Tiqva (IL)

(72) Inventors: Eli Aharoni, Tel Aviv (IL); Vladimir Belousov, Tzur Yitzhak (IL); Yogev Yadid, Kadima (IL)

(73) Assignee: Samsara Vision Ltd., Petah Tiqva (IL)

( * ) Notice: Subject to any disclaimer, the term of this patent is extended or adjusted under 35 U.S.C. 154(b) by 0 days.

(21) Appl. No.: 18/465,323

(22) Filed: Sep. 12, 2023

(51) Int. Cl.
*A61F 2/16* (2006.01)
(52) U.S. Cl.
CPC .......... *A61F 2/16* (2013.01); *A61F 2002/169* (2015.04); *A61F 2220/0008* (2013.01); *A61F 2230/0006* (2013.01)
(58) Field of Classification Search
CPC ............ A61F 2/1648; A61F 2002/1681; A61F 2002/16902; A61F 2002/16903; A61F 2/16
See application file for complete search history.

(56) References Cited

U.S. PATENT DOCUMENTS

| | | | |
|---|---|---|---|
| 11,826,244 B2* | 11/2023 | Kojima | A61F 2/1662 |
| 2005/0113914 A1* | 5/2005 | Miller | A61F 2/1629 |
| | | | 623/6.37 |
| 2017/0000602 A1* | 1/2017 | Sohn | A61F 2/1648 |
| 2021/0370065 A1* | 12/2021 | Mendelewicz | A61F 2/16 |

FOREIGN PATENT DOCUMENTS

WO    WO-2019106011 A1 *  6/2019

* cited by examiner

*Primary Examiner* — Melanie R Tyson
*Assistant Examiner* — Yasniary De La Caridad Morales
(74) *Attorney, Agent, or Firm* — Dekel Patent Ltd.; David Klein

(57) ABSTRACT

An intraocular assembly includes a sulcus fixation frame including at least one anterior haptic restraint member to which a posterior intraocular device receiving member is coupled by means of coupling members. The at least one anterior haptic restraint member includes a sulcus support portion, configured to be received in a sulcus of an eye, and haptic support portions, configured to block anterior movement of haptics of an intraocular device mounted in the sulcus fixation frame or fixate an IOL in the sulcus.

19 Claims, 17 Drawing Sheets

SULCUS FIXATION FRAME

FIELD OF THE INVENTION

The present invention relates generally to intraocular devices, and particularly to a sulcus fixation frame for supporting intraocular devices.

BACKGROUND OF THE INVENTION

An intraocular lens (IOL) is most often placed in the capsular bag so that the natural bag that held the human lens now holds the (IOL). However, there are conditions in which IOL implantation in the capsular bag is not an option, such as a lens exchange procedure, where there is inadequate capsular support, the bag is damaged or remnants of the bag interfere with IOL implantation or other situations in which IOL implantation in the capsular bag is impossible. Other examples of such conditions include subluxation or dislocation of the lens (ectopia lentis) or cases of post-surgical aphakia due to intracapsular cataract extraction surgery, or complications of cataract surgery such as bag dialysis, zonular dialysis, loose zonules, and large posterior capsular rupture, or if an IOL had been placed in the bag previously.

When IOL implantation in the capsular bag is not an option, the IOL may be placed in the ciliary sulcus (or simply the sulcus), which is the space between the posterior surface of the base of the iris and the anterior surface of the ciliary body.

Galilean Implantable Telescopes are designed to correct problems stemming from central field defects, such as those caused by macular degeneration (e.g., atrophic or exudative), chorioretinitis of the macula, central serous chorioretinopathy, or ischemia, for example.

The need for an Implantable Telescope often arises after a regular IOL has already been implanted. It is difficult and possibly damaging to remove the regular IOL after years of use and implant in its place an Implantable Telescope. Therefore, a patient who already has undergone cataract surgery and has an IOL in the capsular bag must pass a lens exchange procedure as mentioned above.

Placing haptics of an Implantable Telescope in the sulcus like suturing an IOL is not considered a solution, because the Implantable Telescope is very sensitive to decentration (misalignment with the central optic axis of the eye) and tilting (angular displacement of the focus of the Implantable Telescope). The tendency for decentration and tilting increases when the IOL is implanted in the sulcus. Thus, prior art placement of the Implantable Telescope in the sulcus does not solve these problems.

SUMMARY

The present invention seeks to provide a sulcus fixation frame for supporting intraocular devices, as described in detail below. The sulcus fixation frame of the invention sits firmly in the sulcus and minimizes or eliminates any problems of decentration and tilting of an IOL. The sulcus fixation frame restrains anterior and posterior movement of the IOL. The sulcus fixation frame of the invention can be used not just to mount an Implantable Telescope, but can be used to mount any kind of IOL or other intraocular device, such as when capsular bag fixation is not an option.

There is provided in accordance with a non-limiting embodiment of the invention an intraocular assembly including a sulcus fixation frame including at least one anterior haptic restraint member to which a posterior intraocular device receiving member is coupled by means of coupling members, the at least one anterior haptic restraint member including a sulcus support portion, configured to be received in a sulcus of an eye, and haptic support portions, configured to block anterior movement of haptics of an intraocular device mounted in the sulcus fixation frame.

BRIEF DESCRIPTION OF DRAWINGS

The present invention will be understood and appreciated more fully from the following detailed description, taken in conjunction with the drawings in which.

DETAILED DESCRIPTION

Figure 1A:
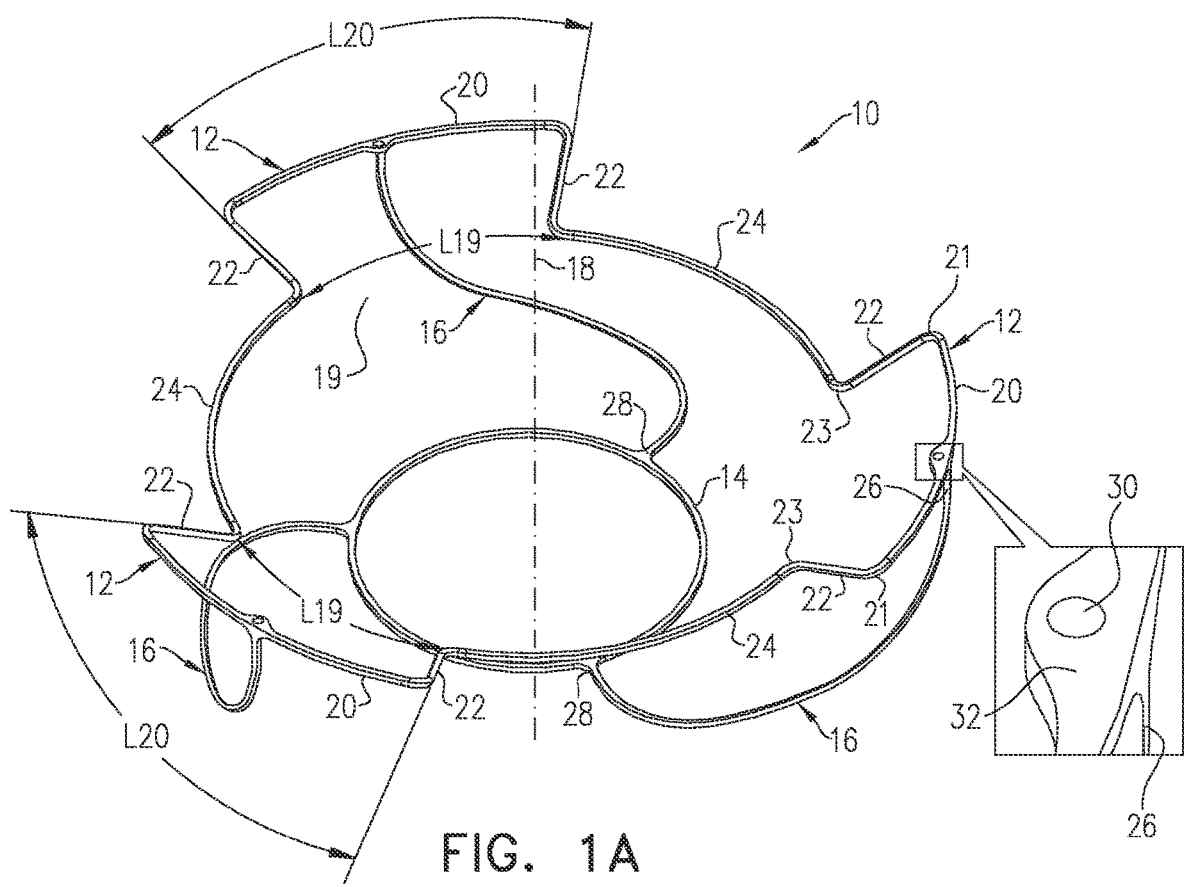
FIG. 1A is a simplified perspective illustration of a sulcus fixation frame, in accordance with a non-limiting embodiment of the invention.
Figure 1B:
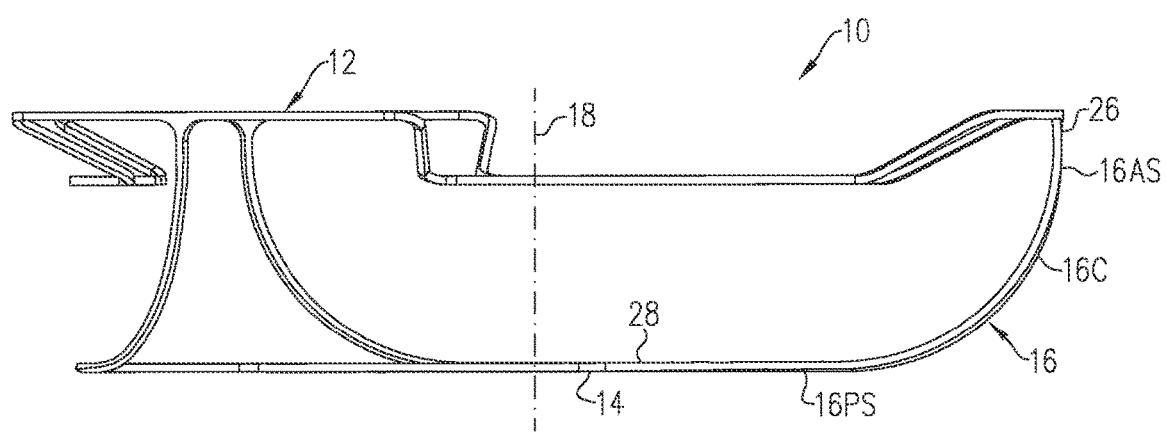
FIGS. 1B and 1C are sagittal and anterior views, respectively, of the sulcus fixation frame.
Figure 1C:
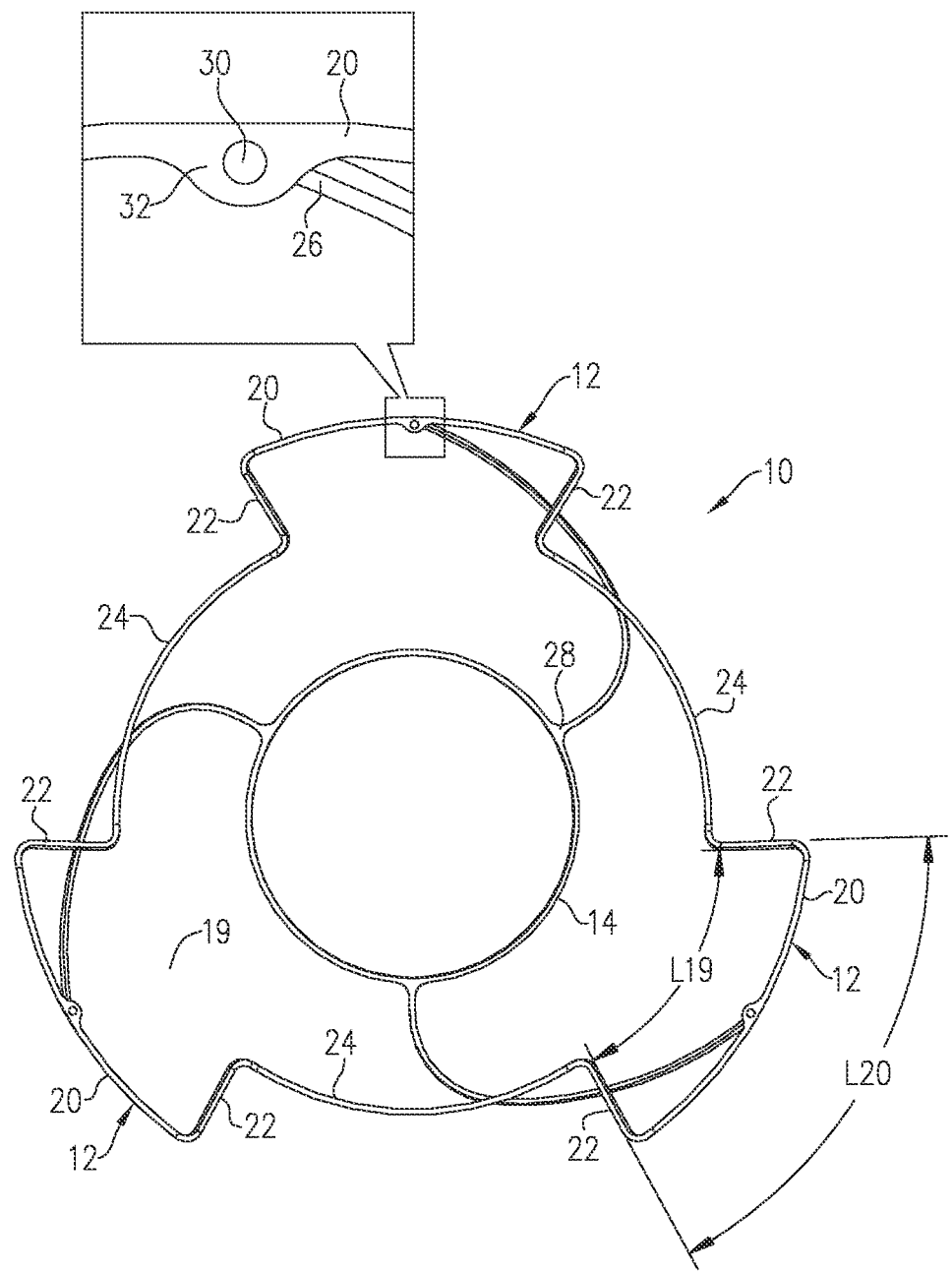

Reference is now made to FIGS. 1A, 1B and 1C, which illustrate a sulcus fixation frame 10, in accordance with a non-limiting embodiment of the invention.

The sulcus fixation frame 10 may include anterior haptic restraint members 12 to which a posterior intraocular device receiving member 14 is coupled by means of coupling members 16. The anterior haptic restraint members 12, posterior intraocular device receiving member 14 and coupling members 16 may be made of slender members, such as wire or filament of any cross-section, round or not round, of any suitable thickness, and may be made of any suitable biocompatible material, such as but not limited to, nitinol, stainless steel, or other metals, or polymeric materials, whether opaque, translucent or transparent.

In the non-limiting illustrated embodiment, the anterior haptic restraint members 12 are circumferentially spaced from each other symmetrically about a central anterior-posterior axis 18 (FIGS. 1A and 1B) of the sulcus fixation frame 10 (anterior and posterior being defined to correspond to the central anterior-posterior axis of the eye in which the frame will be mounted). In the non-limiting illustrated embodiment, there are three anterior haptic restraint members 12 spaced 120° from each other, but other numbers of anterior haptic restraint members and other spacing orientations, including non-symmetrical, are also in the scope of the invention.

In the non-limiting illustrated embodiment, each anterior haptic restraint member 12 includes a radially-outer circumferential support portion 20 that extends between outer ends 21 of a pair of radial portions 22. A radially-inner circumferential support portion 24 extends between inner ends 23 of each pair of radial portions 22. The radially-outer circumferential support portion 20 is also referred to as sulcus support portion 20 and is configured to be received in the sulcus of the eye. The radially-inner circumferential support portion 24 is also referred to as haptic support portion 24 and is configured to block anterior movement of an intraocular device's haptic, as described below.

As seen in FIGS. 1A and 1C, the radially-outer circumferential support portion 20 is circumferentially longer than a circumferential gap 19 between adjacent radially-inner circumferential support portions 24; that is, the circumferential length L20 is greater than the circumferential length L19. In other words, in a sagittal plane, the pair of radial portions 22 tilt towards each other when view in the sagittal views of FIGS. 3C and 3D. An advantage of this structure is that the sulcus fixation frame is firmly received in the sulcus and the intraocular device is firmly mounted in the sulcus fixation frame.

The posterior intraocular device receiving member 14 may be circular as shown, but may alternatively have other shapes, such as but not limited to, elliptic, polygonal and irregular shapes.

Each coupling member 16 may have an anterior end 26 coupled to the radially-outer circumferential support portion 20 and a posterior end 28 coupled to the perimeter of the posterior intraocular device receiving member 14. The anterior end 26 may be coupled to the middle of the radially-outer circumferential support portion 20. Each radially-outer circumferential support portion 20 may include a suture receiving member 30, such as an aperture formed through a tab 32 (alternatively, instead of an aperture, the suture receiving member 30 could be a crevice or notch or other suitable structure). The anterior end 26 may be coupled to the radially-outer circumferential support portion 20 near suture receiving member 30. Tab 32 is part of the radially-outer circumferential support portion 20 and may protrude radially inwards.

It has been surprisingly found that coupling the anterior end 26 to the radially-outer circumferential support portion 20 at suture receiving member 30 provides optimal structural stability for the frame and the intraocular device mounted in the frame. However, the invention is not limited to this arrangement, and it may be preferred in certain applications to couple the anterior end 26 to a different portion of the radially-outer circumferential support portion 20.

As seen in FIG. 1B, each coupling member 16 may have an anterior straight portion 16AS extending from the anterior end 26, followed by a curved portion 16C and ending in a posterior straight portion 16PS that extends to the posterior end 28.

The invention is not limited to any size or dimensions. The sulcus of the human eye may have a diameter in the range of 11 mm±0.4 mm, so the overall diameter of the sulcus fixation frame, which is the outer diameter of the diameter of anterior haptic restraint members 12 (that is, the outer edge of the radially-outer circumferential support portions 20), may be accordingly about 11 mm±0.4 mm. The diameter of a dilated human iris can be at the max in the range of 7-7.5 mm. Without limitation, an IMT which may be mounted in the sulcus fixation frame, has an anterior-posterior axial length of 4.4 mm, a central optic with a diameter of 3.6 mm, and haptics with an outer diameter of 10.8 mm. Accordingly, without limitation, the diameter of the radially-inner circumferential support portions 24 may be 8 mm so as not to visually interfere with the field of view of the eye even when the iris is dilated, and yet block the haptics from anterior movement. The diameter of the posterior intraocular device receiving member 14 may be 4-4.2 mm so that the central optic, which is received in the posterior intraocular device receiving member 14, has radial clearance. It is noted that the outer ends 21 and the inner ends 23 of radial portions 22 are hidden under the IMT haptics, too.

Reference is now made to FIGS. 2A-3H, which illustrate a method for implanting the sulcus fixation frame 10 in the sulcus. The fixation may be done by sutures fixated to the sclera by any method, although a preferred method is a flanging method.

However, the invention is not limited to this technique and the sulcus fixation frame may be mounted in the sulcus by other means.

Figure 2A:
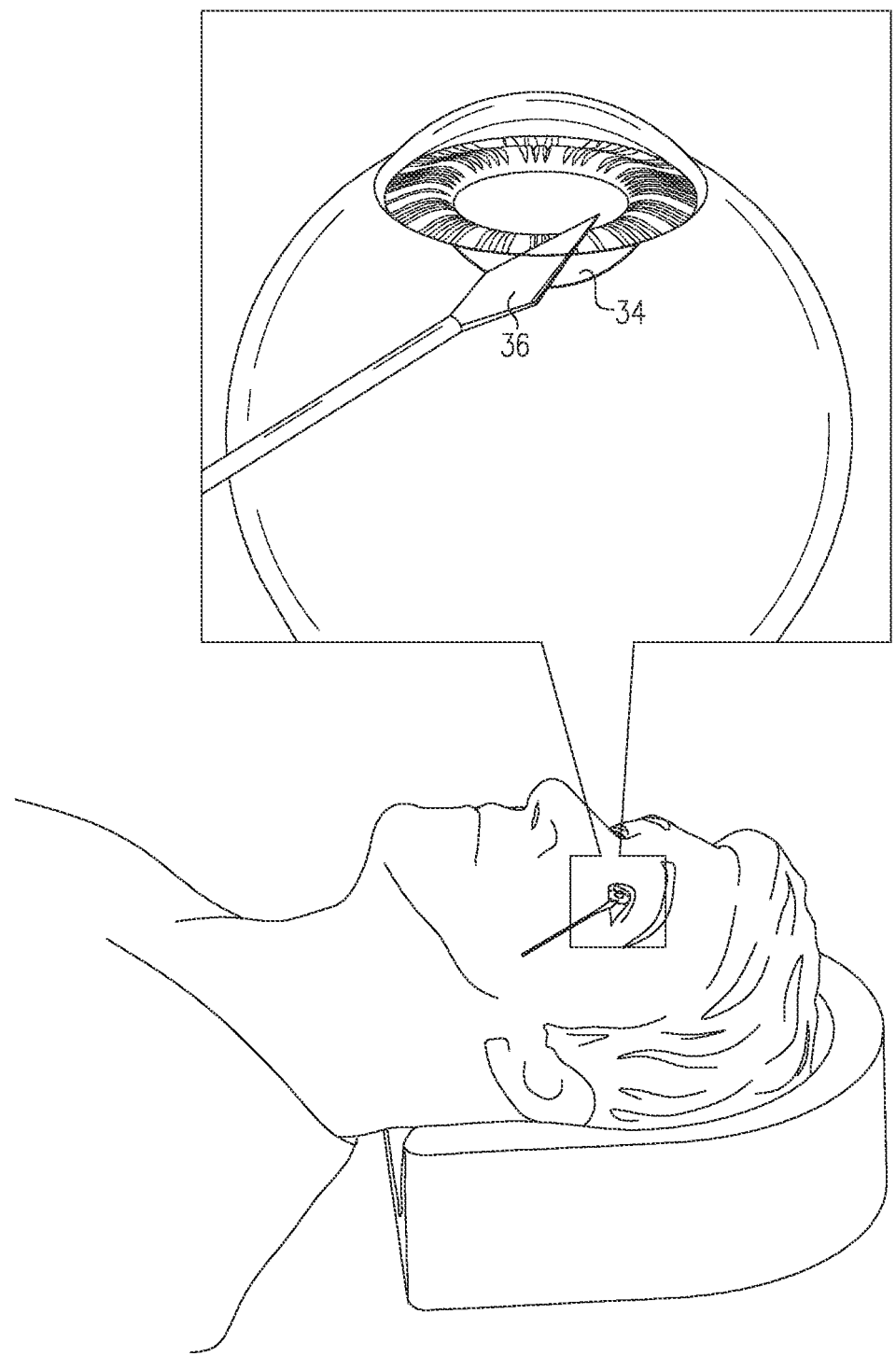
FIG. 2A is a perspective illustration of an initial limbal incision, which is part of a method for implanting the sulcus fixation frame, in accordance with a non-limiting embodiment of the invention.
Figure 2B:
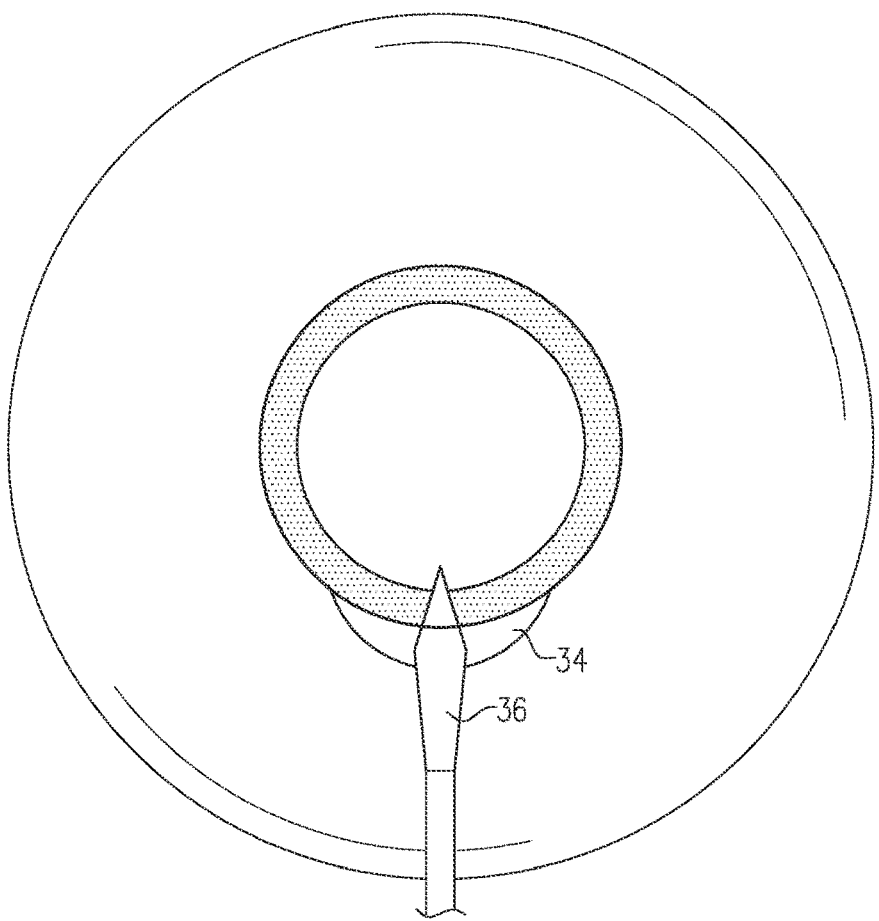
FIG. 2B is an anterior view of the limbal incision.

In FIG. 2A, an initial limbal incision 34 may be made with a cutting tool 36, such as a keratome. FIG. 2B is an anterior view of the limbal incision 34.

Figure 2C:
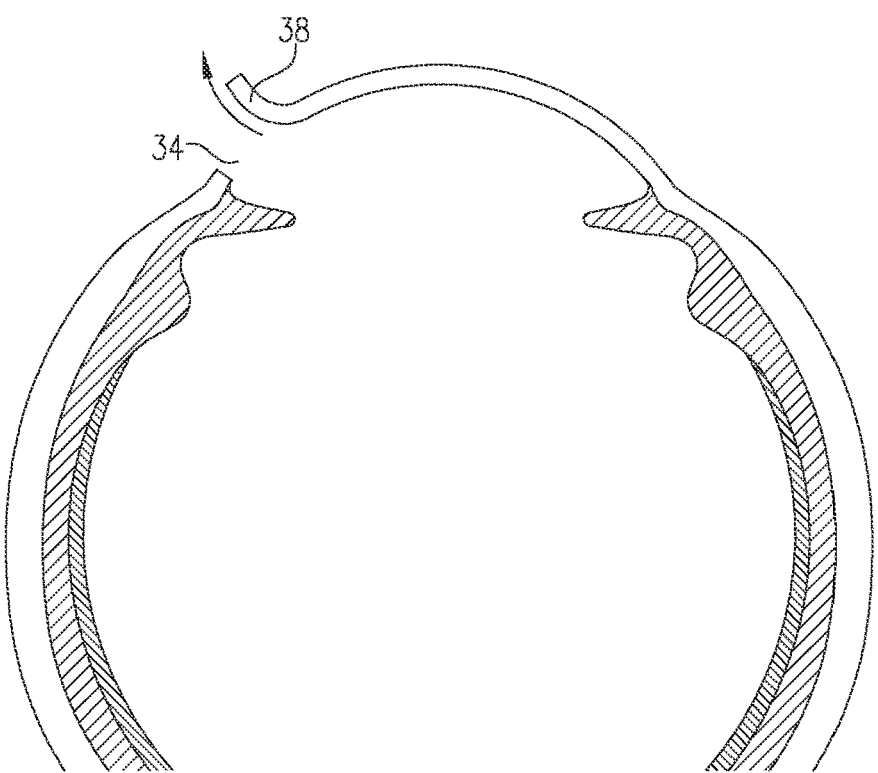
FIG. 2C is a sagittal view of raising the corneal flap created by the limbal incision.

FIG. 2C illustrates raising a corneal flap 38 created by the limbal incision 34 to create an entry opening for the frame.

Figure 3A:
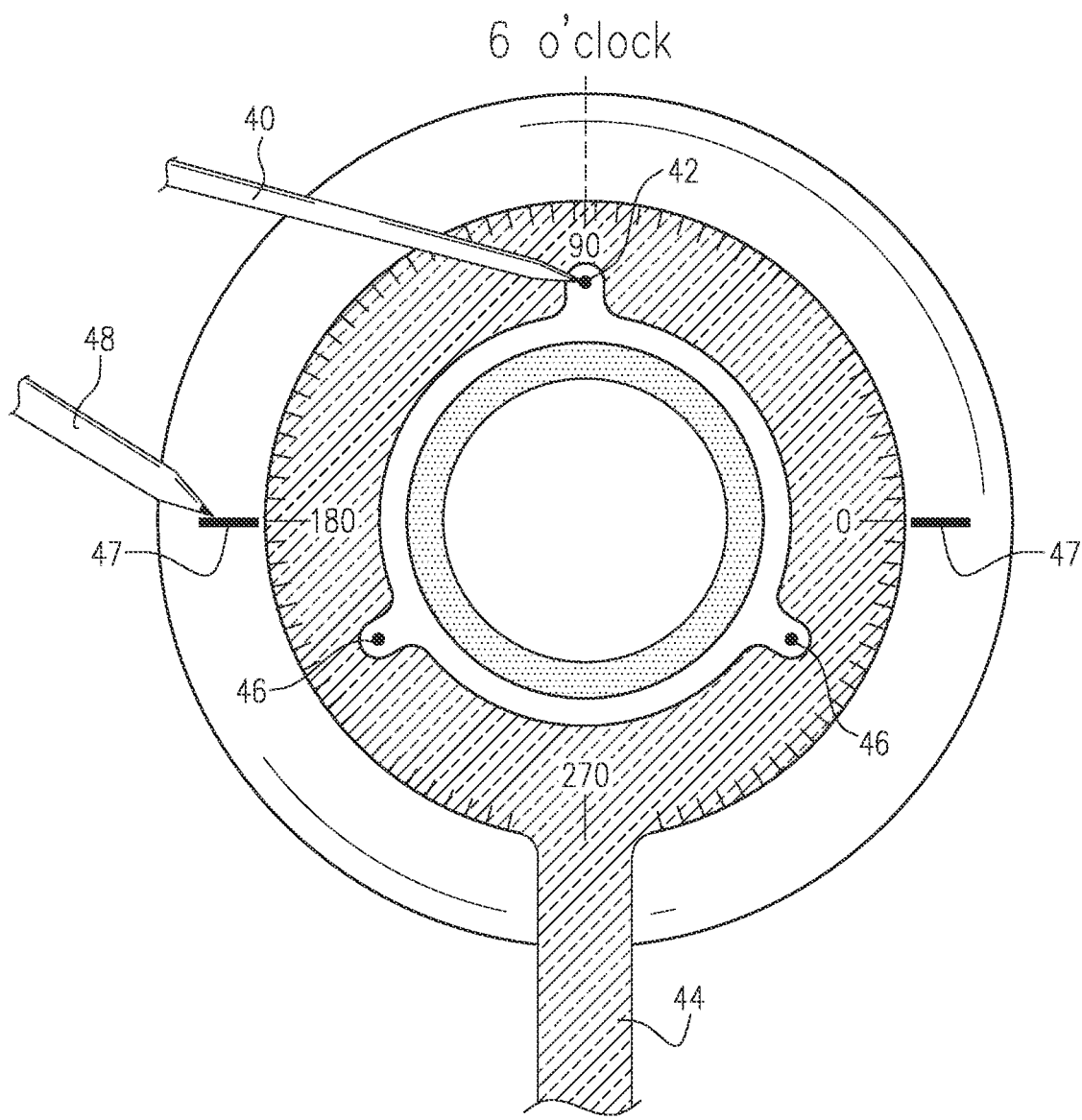
FIG. 3A is an anterior view illustration of making a sclerotomy incision at the 6 o'clock (18:00) position, using a sclerotomy jig tool, which has guide holes for making sclerotomies at the 10, 2 and 6 o'clock (10:00, 14:00, 18:00) or other divisional positions.

FIG. 3A illustrates a biocompatible marking pencil 40 being used to mark the sclerotomy puncture 42 posterior to the limbus and pierced into the vitreous space at the 0600 o'clock or other divisional position. A sclerotomy jig tool 44 may be used as well to mark the guide sockets 46 that mark all sclerotomies at the 4, 8 and 12 o'clock or other divisional positions. The sclerotomy jig tool 44 may have angular graduations for showing angles from 0-360°. A marker pencil 48 may also be used to mark twin marks 47 on the sclera that adequately will be parallel to the twin marks that describe the astigmatic portion on the toric IOLs.

Figure 3B:
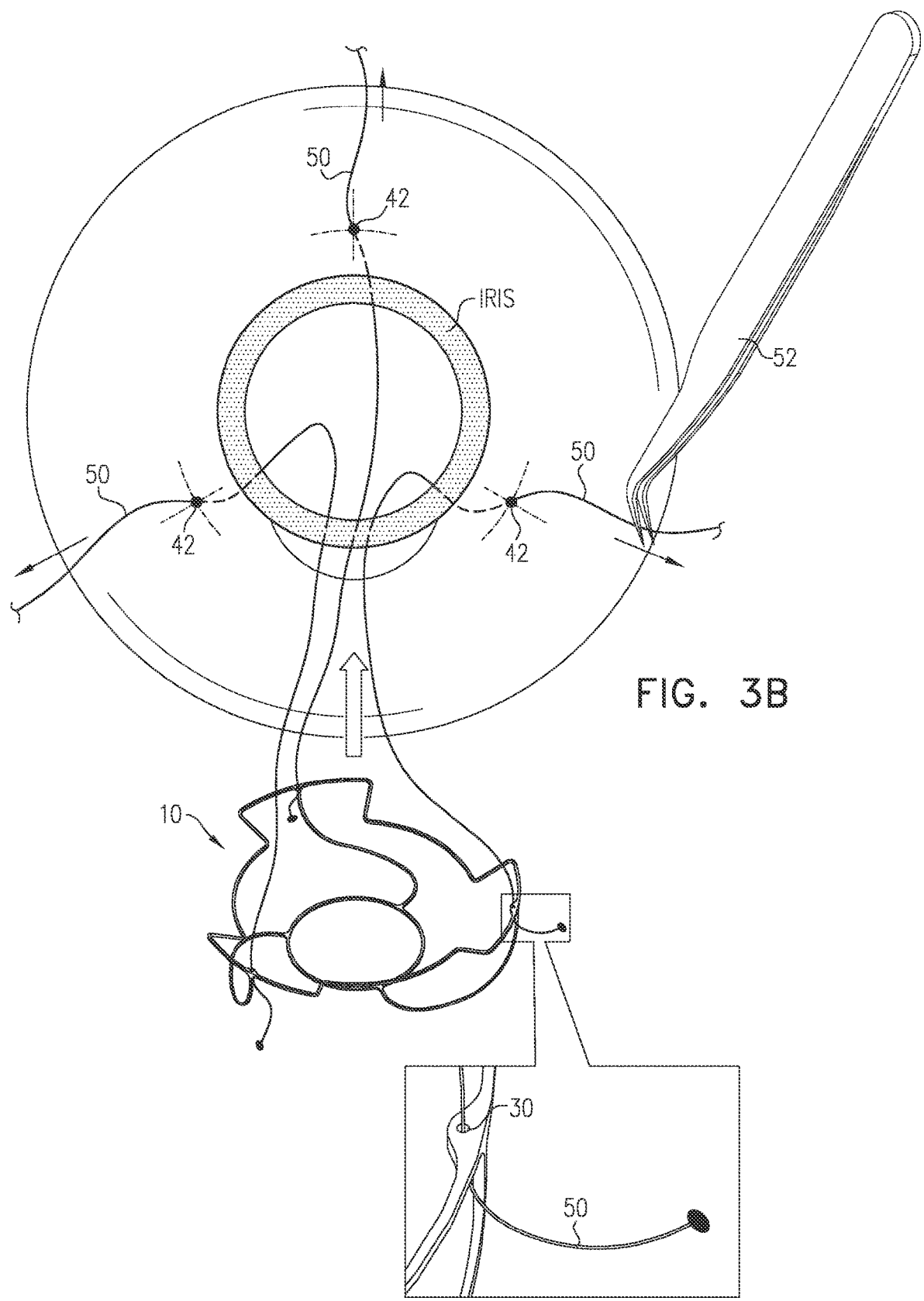
FIG. 3B is an anterior view illustration of threading sutures through the sclerotomies that have been made at the 10, 2 and 6 o'clock (10:00, 14:00, 18:00) positions, the sutures being coupled to the sulcus fixation frame.

FIG. 3B illustrates threading sutures 50 through the sclerotomy incisions 42 that have been made at the 10, 2 and 6 o'clock (10:00, 14:00, 18:00). Sutures 50 are coupled to the sulcus fixation frame 10 at suture receiving members 30. The sutures 50 may be manipulated by forceps (also called tweezers) 52. Sutures 50 may be made of nylon or polypropylene (such as PROLENE sutures), or any other suitable material.

Figure 3C:
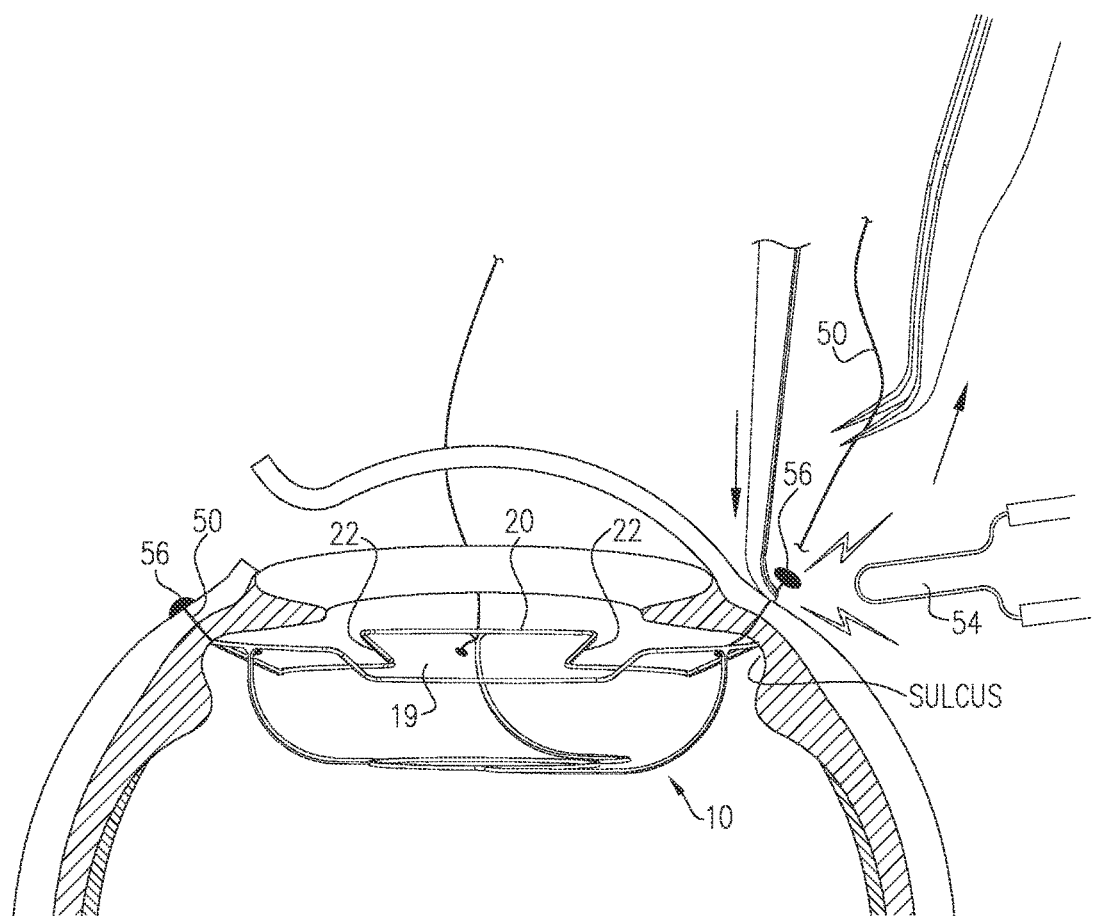
FIG. 3C is a sagittal view illustration of cutting excess suture and using a handheld cautery to create a flange or bulb at the tip of the suture near the sclera to secure the sulcus fixation frame in the sulcus.

FIG. 3C illustrates cutting excess suture and using a handheld cautery 54 to create a flange or bulb 56 at the tip of the suture 50 near the sclera to secure the sulcus fixation frame 10 in the sulcus.

Figure 3D:
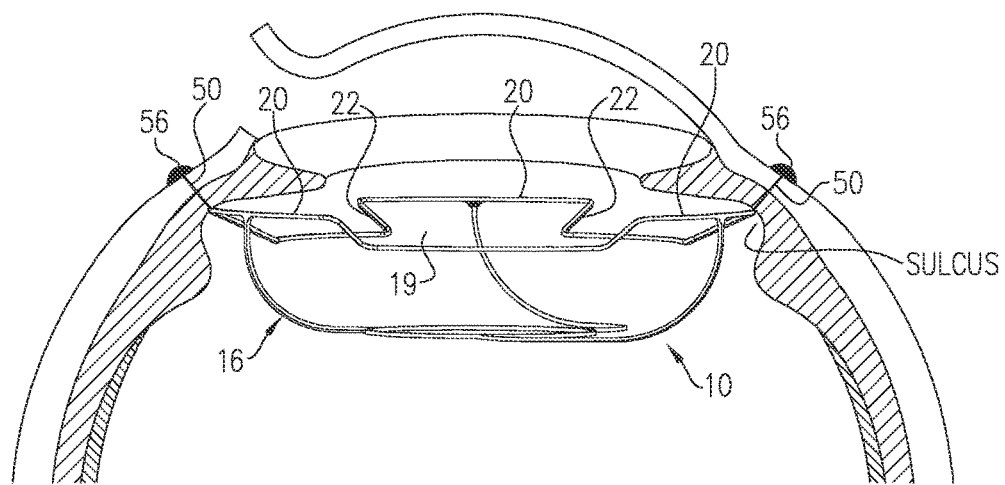
FIG. 3D is a sagittal view illustration of the sulcus fixation frame secured in the sulcus.

FIG. 3D illustrates the sulcus fixation frame 10 secured in the sulcus.

Figure 3E:
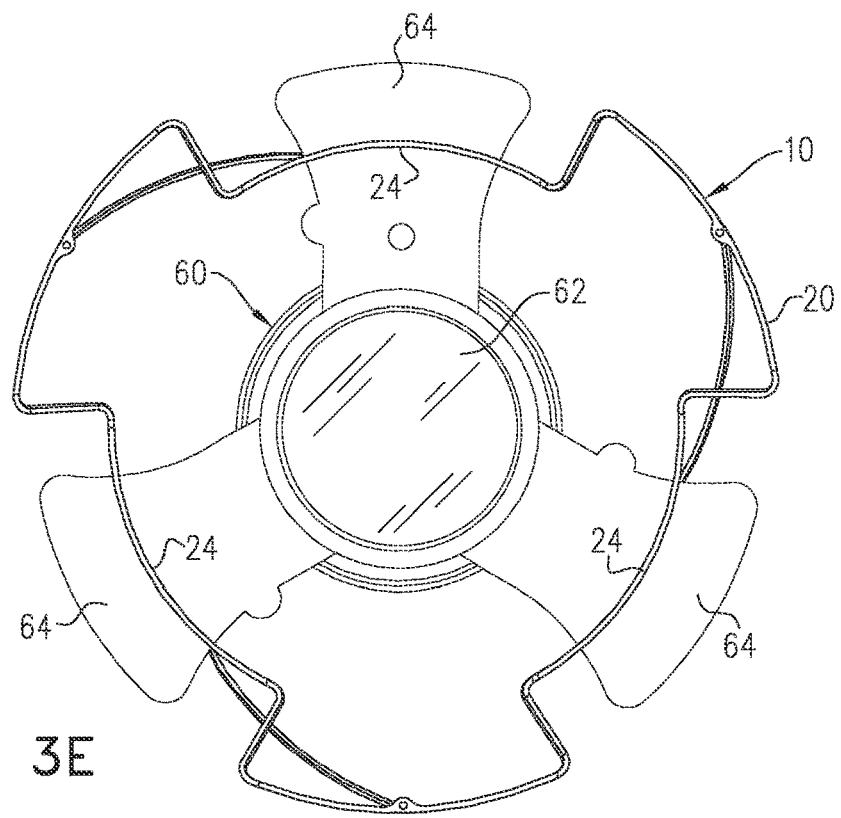
FIG. 3E is an anterior view of an Implantable Telescope (in this exemplary case, an IMT—implantable miniature telescope) held in the sulcus fixation frame.
Figure 3F:
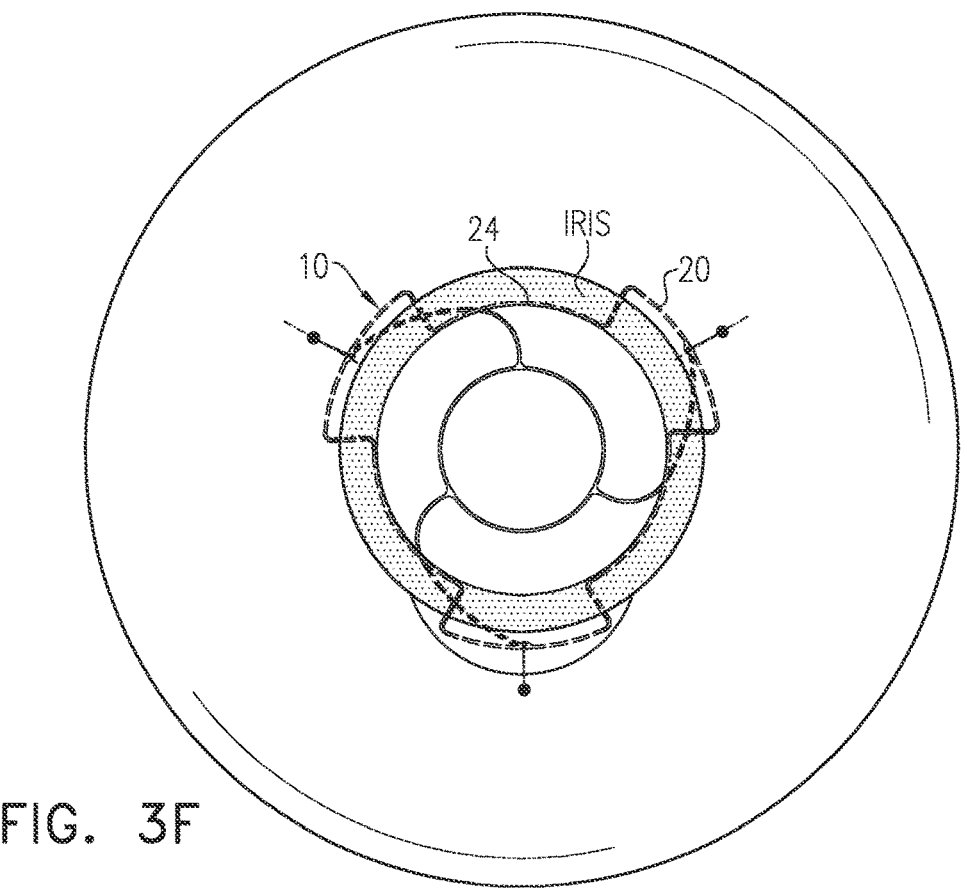
FIG. 3F is an anterior view of the sulcus fixation frame that has been affixed in the sulcus of the eye.
Figure 3G:
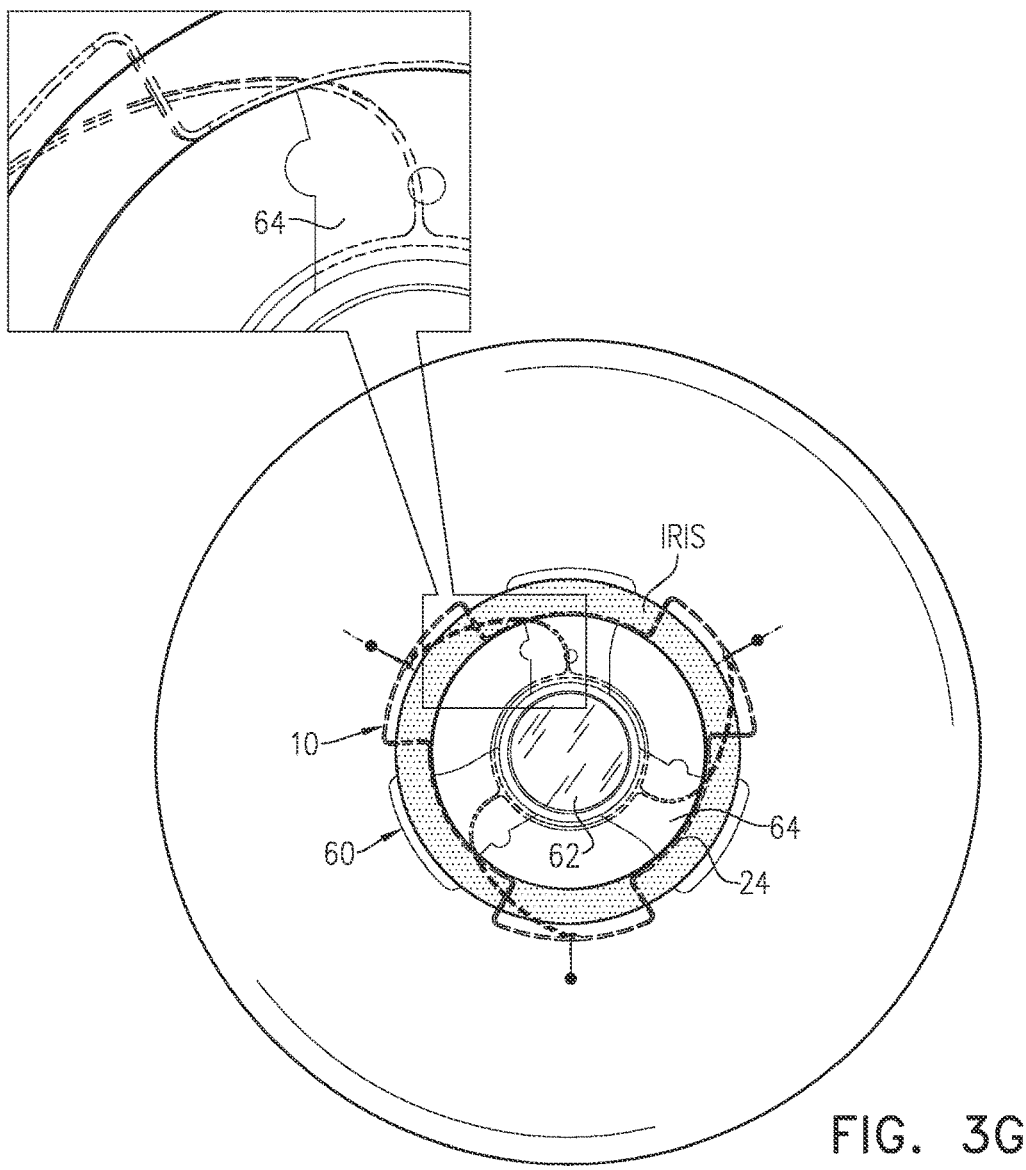
FIGS. 3G and 3H are anterior and sagittal views, respectively, of the Implantable Telescope held in the sulcus fixation frame that has been affixed in the sulcus of the eye.
Figure 3H:
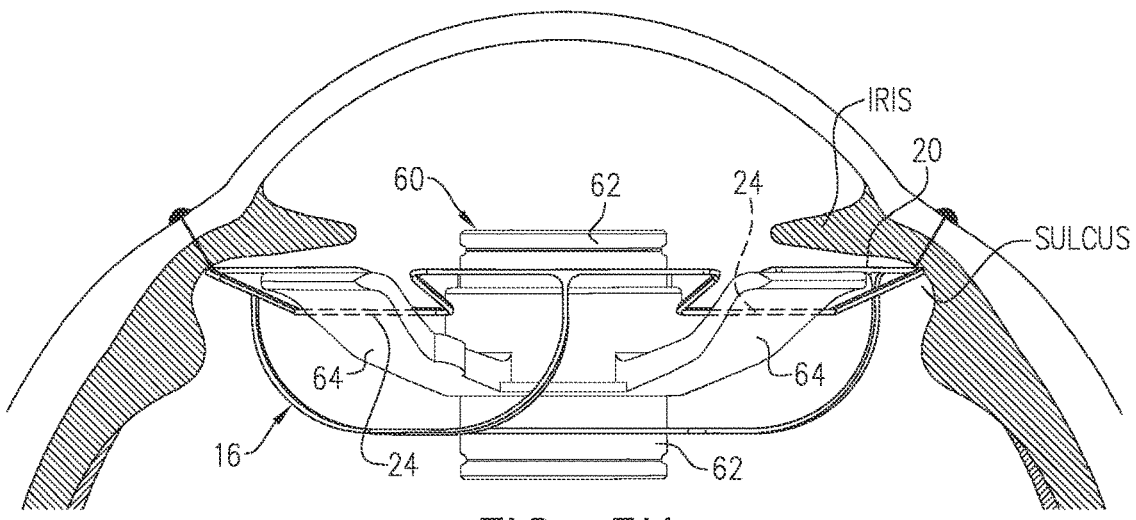

FIG. 3E is an anterior view of an Implantable Telescope 60 (in this exemplary case, an IMT—implantable miniature telescope) held in the sulcus fixation frame 10. Implantable Telescope 60 may have a central optic 62 and (three) haptics 64. FIG. 3F is an anterior view of the sulcus fixation frame 10 that has been affixed in the sulcus of the eye. FIGS. 3G and 3H are anterior and sagittal views, respectively, of the Implantable Telescope 60 held in the sulcus fixation frame 10 that has been affixed in the sulcus of the eye.

It is seen in FIG. 3H that the posterior sides of the radially-inner circumferential support portions 24 (haptic support portions 24) abut against the anterior sides of haptics 64 and thus block the haptics 64 from anterior movement, and do not visually interfere with the field of view when looking from outside into the posterior chamber of the eye. Anterior sides on portions of the coupling members 16 abut against the posterior sides of haptics 64 and thus block the haptics 64 from posterior movement, and do not visually interfere with the field of view when looking by slit lamp examination from outside into the posterior chamber of the eye.

The combination of the good circumferential fit of sulcus support portions 20 in the sulcus and the good anterior-posterior fixation of the haptics 64 by haptic support portions 24 and coupling members 16 help achieve three important results:
  a. The sulcus fixation frame enabling free relaxation of the intraocular lens haptics in the sulcus and minimizes or eliminates any problems of decentration of the IOL.
  b. The sulcus fixation frame enabling free relaxation of the intraocular lens haptics in the sulcus and minimizes or eliminates any problems of tilting of the IOL.
  c. The sulcus fixation frame restrains anterior and posterior movement of the Implantable telescope only.

Again, it is noted that the invention is useful for any intraocular device, and not just IOLs.

Figure 4A:
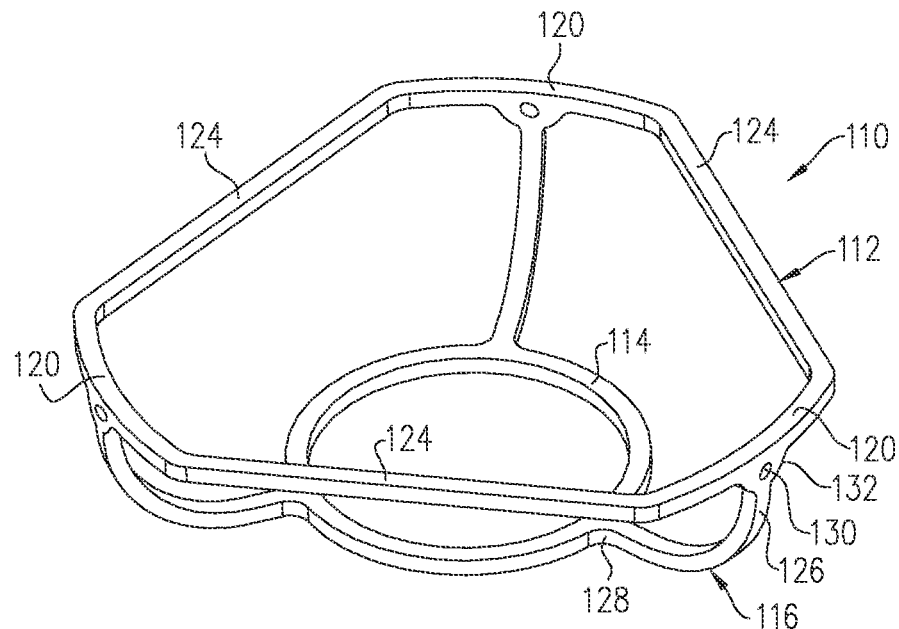
FIG. 4A is a simplified perspective illustration of a sulcus fixation frame, in accordance with another non-limiting embodiment of the invention.
Figure 4B:
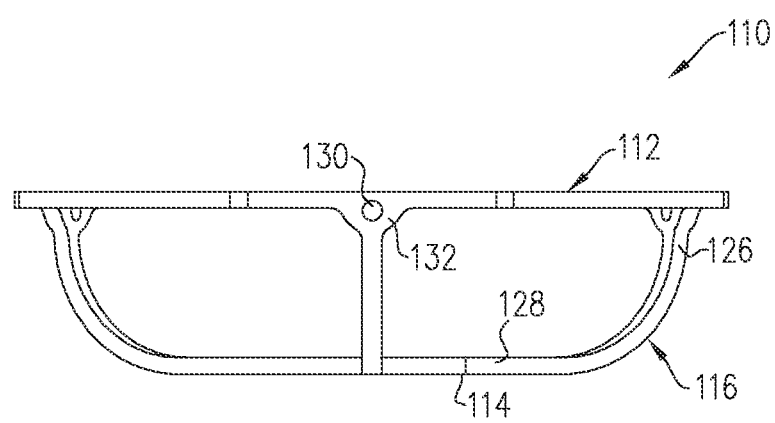
FIGS. 4B and 4C are sagittal and anterior views, respectively, of the sulcus fixation frame.
Figure 4C:
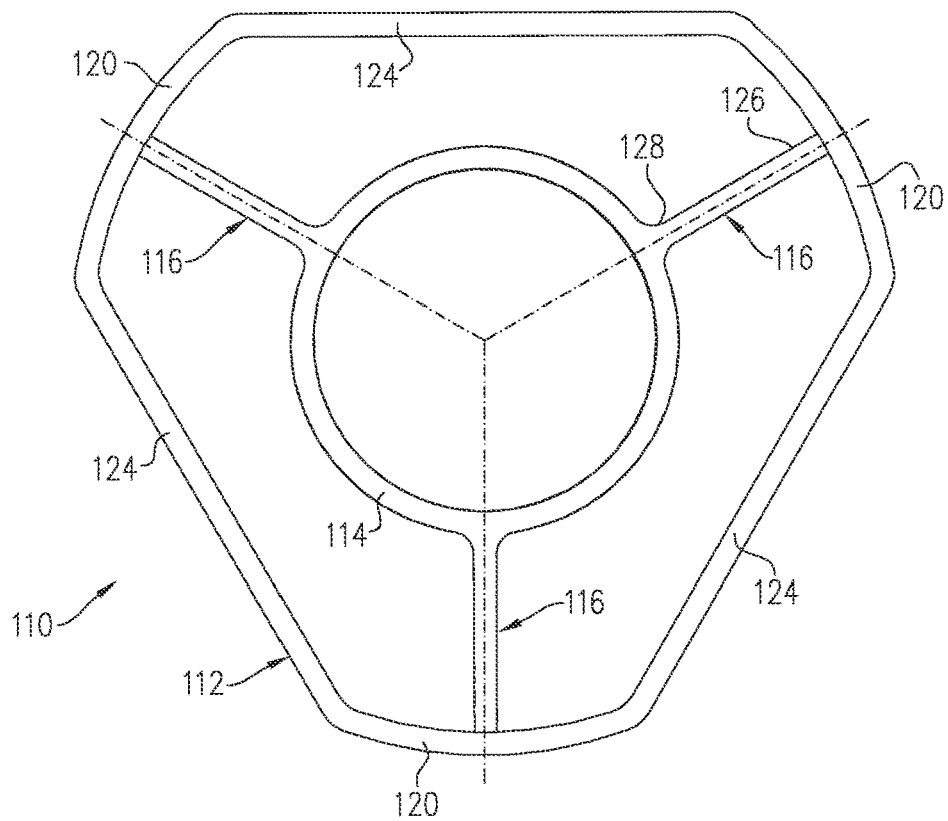

Reference is now made to FIGS. 4A-4C, which illustrate a sulcus fixation frame 110, in accordance with another non-limiting embodiment of the invention.

The sulcus fixation frame 110 may include anterior haptic restraint members 112 to which a posterior intraocular device receiving member 114 is coupled by means of coupling members 116. As with other embodiments, the anterior haptic restraint members 112, posterior intraocular device receiving member 114 and coupling members 116 may be made of slender members, such as wire or filament of any cross-section, round or not round, of any suitable thickness, and may be made of any suitable transparent biocompatible material, such as transparent polymeric materials which will not block the field of view of the eye.

In the non-limiting illustrated embodiment, there are three anterior haptic restraint members 112 spaced 120° from each other, but other numbers of anterior haptic restraint members and other spacing orientations, including non-symmetrical, are also in the scope of the invention.

In the non-limiting illustrated embodiment, each anterior haptic restraint member 112 includes a sulcus support portion 120, which may be curved. The sulcus support members 120 are configured to be received in the sulcus of the eye. The sulcus support portions 120 may be coupled to each other by haptic support portions 124, which are configured to block anterior movement of the haptic. The haptic support portions 124 may be straight.

Each coupling member 116 may have an anterior end 126 coupled to the sulcus support portion 120 and a posterior end 128 coupled to the perimeter of the posterior intraocular device receiving member 114. The anterior end 126 may be coupled to the middle of the sulcus support portion 120. Each sulcus support portion 120 may include a suture receiving member 130, such as an aperture formed through a tab 132 (alternatively, instead of an aperture, the suture receiving member 130 could be a crevice or notch or other suitable structure). Tab 132 may protrude towards the posterior direction.

Figure 4D:
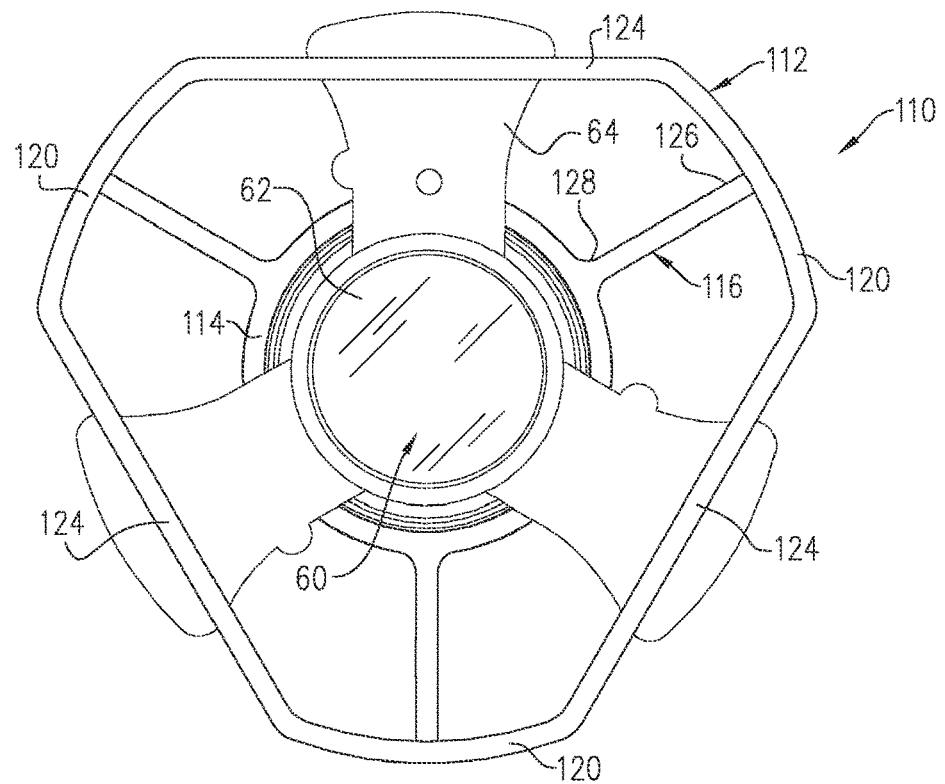
FIG. 4D is an anterior view of an Implantable Telescope held in the sulcus fixation frame of FIGS. 4A-4C.

FIG. 4D is an anterior view of Implantable Telescope 60 held in the sulcus fixation frame 110. The haptic support portions 124 block anterior movement of the haptics 64.

Figure 5A:
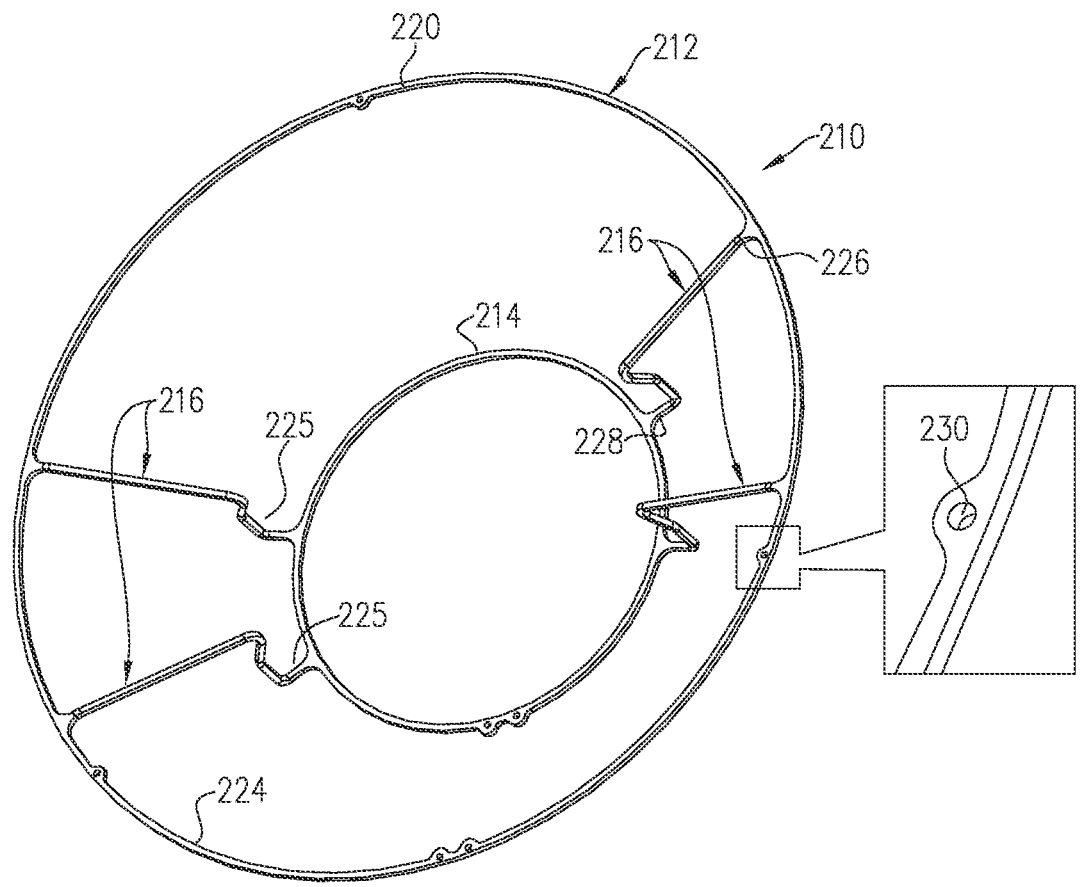
FIG. 5A is a simplified perspective illustration of a sulcus fixation frame, in accordance with yet another non-limiting embodiment of the invention.
Figure 5B:
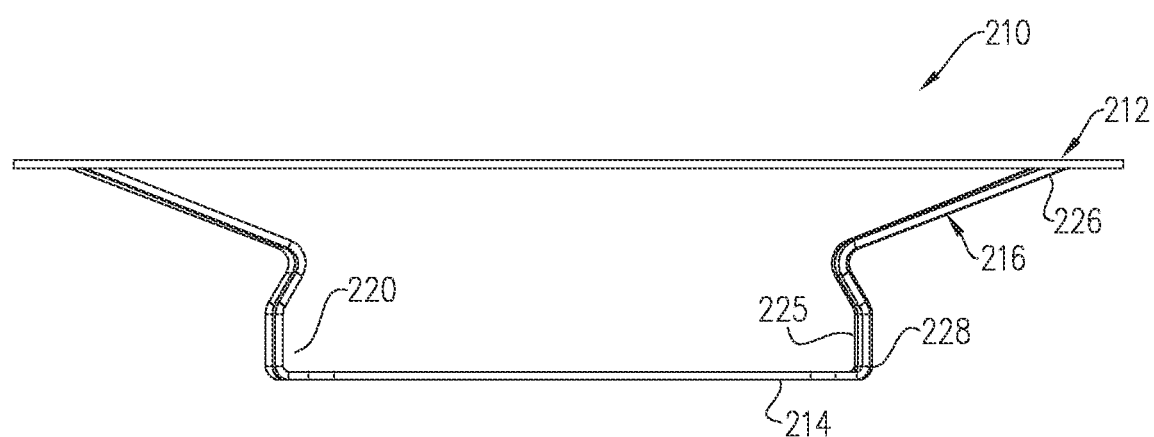
FIGS. 5B and 5C are sagittal and anterior views, respectively, of the sulcus fixation frame.
Figure 5C:
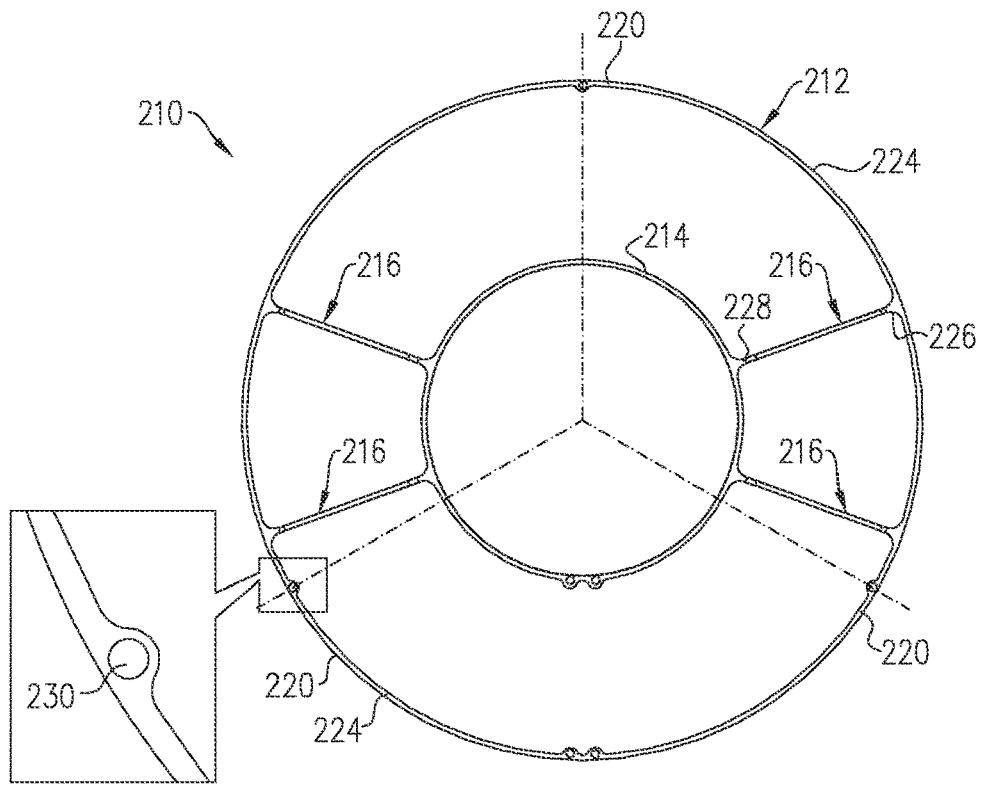

Reference is now made to FIGS. 5A-5C, which illustrate a sulcus fixation frame 210, in accordance with another non-limiting embodiment of the invention.

The sulcus fixation frame 210 may include an anterior haptic restraint member 212 to which a posterior intraocular device receiving member 214 is coupled by means of coupling members 216. As with other embodiments, the anterior haptic restraint member 212, posterior intraocular device receiving member 214 and coupling members 216 may be made of slender members, such as wire or filament of any cross-section, round or not round, of any suitable thickness, and may be made of any suitable biocompatible material, such as but not limited to, nitinol, stainless steel, or other metals, or polymeric materials.

In the non-limiting illustrated embodiment, the anterior haptic restraint member 212 is a continuous 3600 (e.g., round) member. The anterior haptic restraint member 212 may include along its circumferential length sulcus support portions 220, configured to be received in the sulcus of the eye, and haptic support portions 224, configured to block anterior movement of the haptic. In this embodiment, the sulcus support portions 220 and the haptic support portions 224 are all along the circumference of the anterior haptic restraint member 212.

Each coupling member 216 may have an anterior end 266 coupled to the anterior haptic restraint member 212 (at or not at the sulcus support portion 220) and a posterior end 228 coupled to the perimeter of the posterior intraocular device receiving member 214. In the non-limiting illustrated embodiment, there are left and right pairs of coupling members 216 on opposite sides of the posterior intraocular device receiving member 214.

Each coupling member 216 may include an intraocular device support member 225, such as a pocket or indentation bent or otherwise formed in coupling member 216.

As in other embodiments, anterior haptic restraint member 212 may include suture receiving members 230.

Figure 5D:
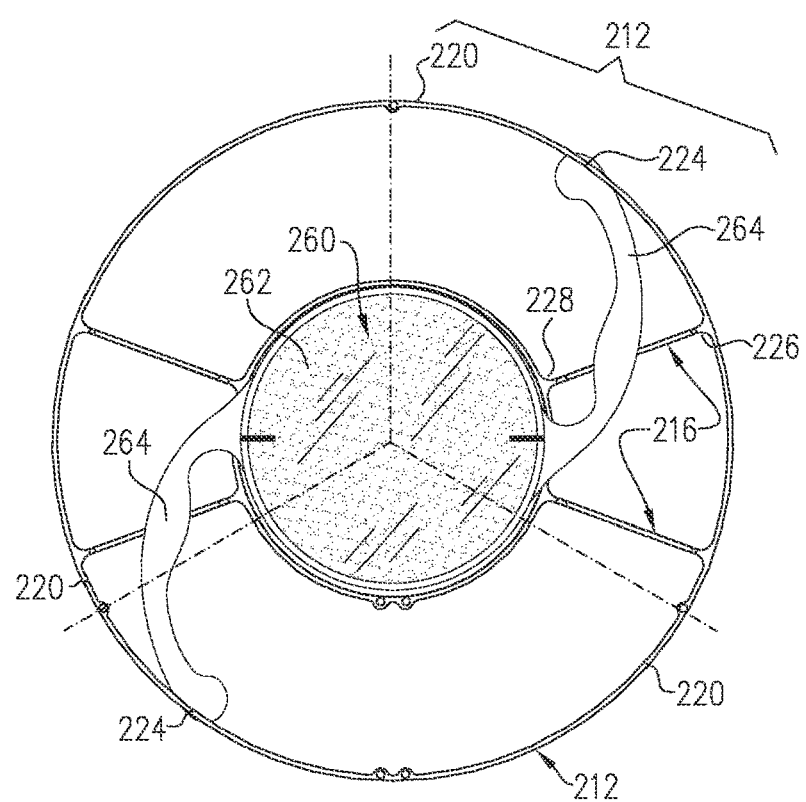
FIG. 5D is an anterior view of an IOL (with dialable haptics) held in the sulcus fixation frame of FIGS. 5A-5C.

FIG. 5D is an anterior view of an IOL 260 held in the sulcus fixation frame 210. IOL 260 may have a central optic 262 and dialable haptics 264, and both side toric mark 266. The haptic support portions 224 situated at the sulcus area and the intraocular device support member 225 stabilize and fixate the IOL from any direction movement and keep it from any decentered or tilt movement.

Figure 5E:
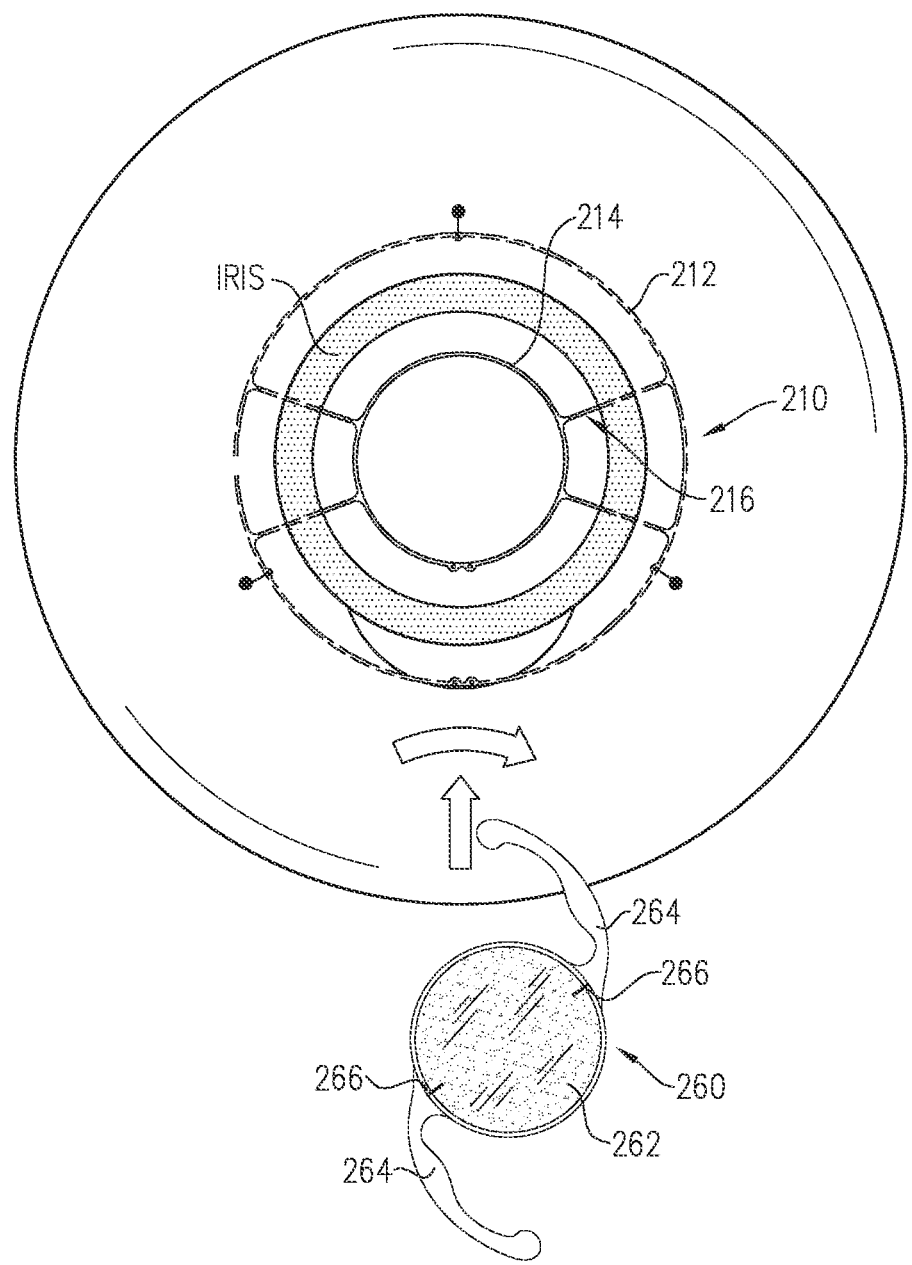
FIG. 5E is an anterior view of the sulcus fixation frame of FIGS. 5A-5C affixed in the sulcus of the eye, and showing the IOL poised to be inserted through a scleral tunnel incision (or corneal incision) for mounting in the sulcus fixation frame.

FIG. 5E is an anterior view of the sulcus fixation frame 210 affixed in the sulcus of the eye, and showing the IOL 260 poised to be inserted through a scleral tunnel incision (or alternatively corneal incision) for mounting in the sulcus fixation frame 260.

Figure 5F:
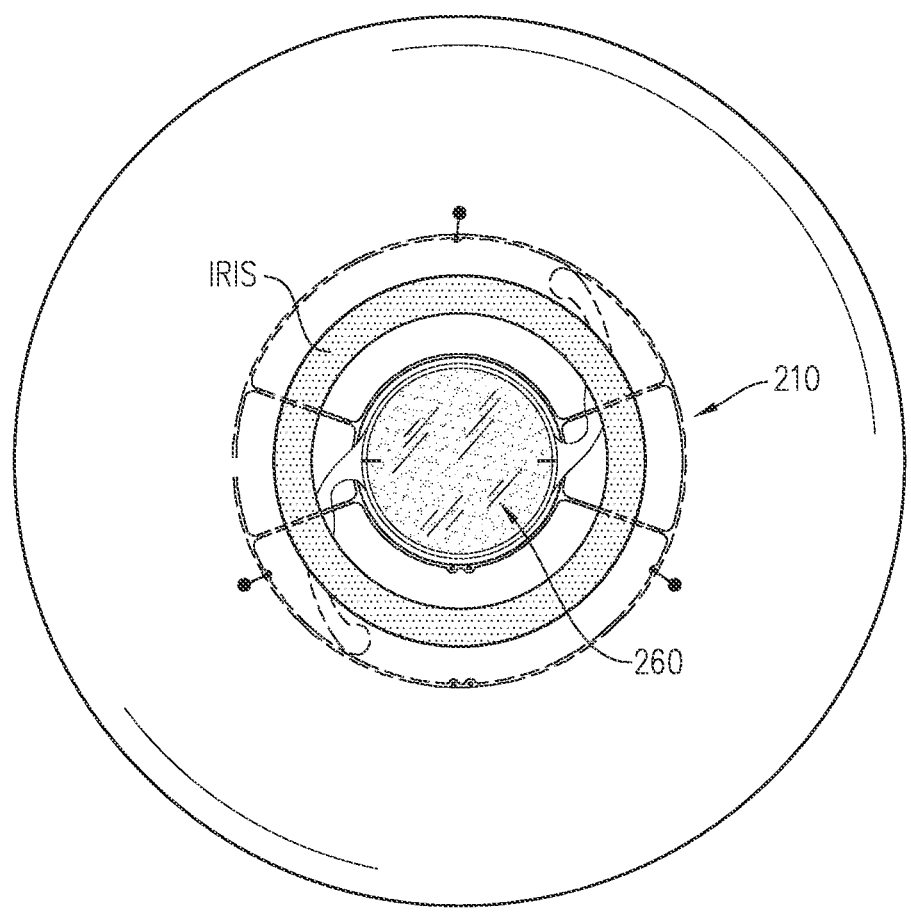
FIG. 5F is an anterior view of the IOL mounted in the sulcus fixation frame in the eye.

FIG. 5F is an anterior view of the IOL 260 mounted in the sulcus fixation frame 210 in the eye. IOL 260 may be a toric IOL.

Toric IOLs have different cylinder in different meridians of the lens to correct the asymmetric cylinder of the eye that is characteristic of astigmatism. Standard toric intraocular lenses are available in cylinder powers of 1.5D to 6.0D. They are usually intended for regular corneal astigmatism in a range from 0.75D to 4.75D and extended series or customized IOLs are available to achieve higher cylindrical power. Toric IOLs are available as monofocal and multifocal lenses. Cataract surgery with toric IOLs is essentially the same as cataract surgery with a conventional IOL, but with a couple of important differences. Prior to surgery, measurements are taken to enable cataract surgeons to choose the most beneficial toric IOL cylinder and the required orientation of the implant in the eye to correct the astigmatism successfully. Toric IOLs have special markers on the peripheral parts of the lens 266 that enable the surgeon to see the orientation of the astigmatism correction in the lens. Once the toric IOL is implanted in the eye, the surgeon then rotates (dials) the lens so the astigmatism correction is properly aligned for best results.

In accordance with an embodiment of the invention, the sulcus fixation frame 210 may be used to mount toric IOL 260 and eliminate the need for dialing the toric IOL 260 after implantation as is now described.

Figure 5G:
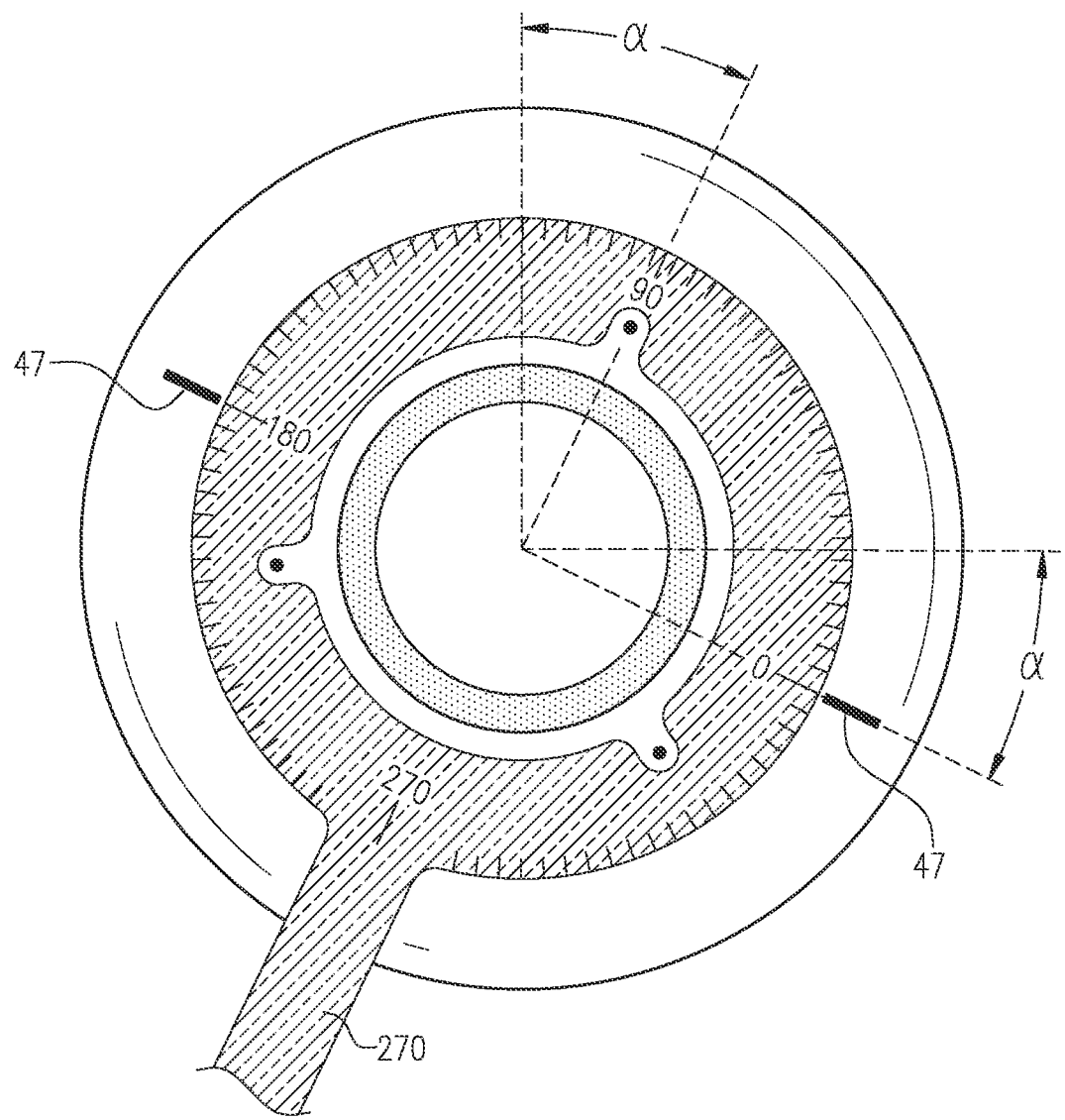
FIG. 5G is an anterior view illustration of a sclerotomy jig tool for use with a toric IOL, in which the tool is used to make the sclerotomy incisions for the sulcus fixation frame at the required dialing angle alpha, which is the required angular orientation of the astigmatism correction provided by the toric IOL, so that the sulcus fixation frame is pre-dialed to the required angular orientation of the astigmatism correction.

Reference is now made to FIG. 5G, which illustrates a sclerotomy jig ruler tool 270 for use with the toric IOL. The sclerotomy jig ruler tool 270 is used to make the sclerotomy incisions for the sulcus fixation frame at the required dialing angle alpha, which is the required angular orientation of the astigmatism correction provided by the toric IOL, so that the sulcus fixation frame is pre-dialed to the required angular orientation (indicated by marks 47) of the astigmatism correction.

Figure 5H:
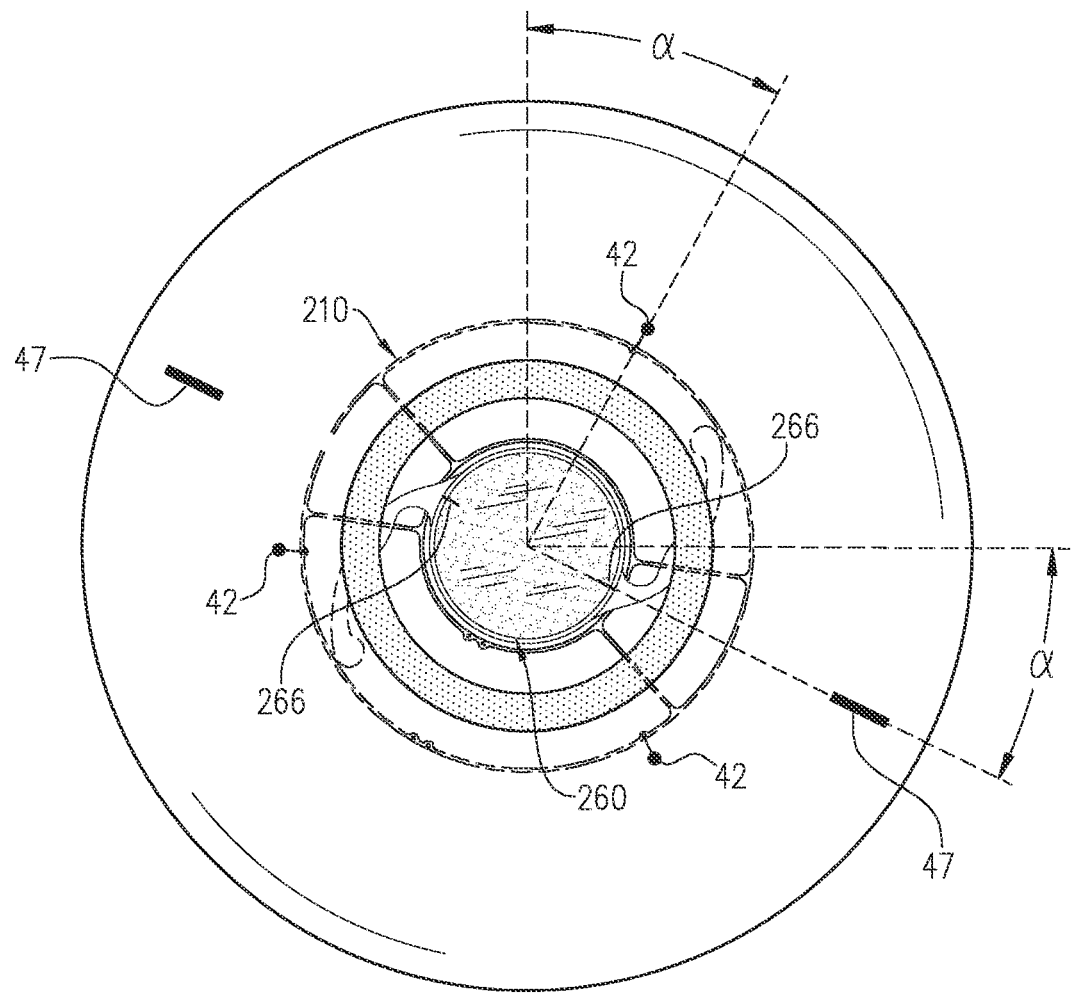
FIG. 5H is an anterior view illustration of the toric IOL mounted in the sulcus fixation frame in the eye, showing that the toric IOL and its haptics are mounted at the required angular orientation of the astigmatism correction, thus eliminating any need to dial the toric IOL after implantation in the sulcus fixation frame.

FIG. 5H illustrates toric IOL 260 mounted in the sulcus fixation frame 210 in the eye, showing that the toric IOL 260 and its haptics are mounted at the required angular orientation of the astigmatism correction 266, thus eliminating any need to dial the toric intraocular lens 260 after implantation in the sulcus fixation frame 210.

What is claimed is:

1. An intraocular assembly comprising:
a sulcus fixation frame comprising at least one anterior restraint member to which a posterior intraocular device receiving member is coupled by means of coupling members, said at least one anterior restraint member comprising a sulcus support portion, configured to be received in a sulcus of an eye, and anterior blocking members, configured to block anterior movement of haptics of an intraocular device mounted in said sulcus fixation frame, wherein said anterior blocking members, said posterior intraocular device receiving member, and said coupling members are slender wires or filaments.

2. The intraocular assembly according to claim 1, wherein said sulcus support portion is curved.

3. The intraocular assembly according to claim 1, wherein said anterior blocking members are curved.

4. The intraocular assembly according to claim 1, wherein said anterior blocking members are straight.

5. The intraocular assembly according to claim 1, wherein said at least one anterior restraint member comprises a plurality of anterior restrain members, each anterior restrain member comprising a sulcus support position, wherein said sulcus support portions are coupled to each other by said anterior blocking members.

6. The intraocular assembly according to claim 1, wherein said at least one anterior restraint member comprises a plurality of anterior restraint members circumferentially spaced from each other symmetrically about a central anterior-posterior axis of said sulcus fixation frame.

7. The intraocular assembly according to claim 1, wherein said sulcus support portion comprises a suture receiving member.

8. The intraocular assembly according to claim 1, wherein each of said coupling members comprises an anterior end coupled to said sulcus support portion and a posterior end coupled to a perimeter of said posterior intraocular device receiving member.

9. The intraocular assembly according to claim 8, wherein each of said coupling members comprises an anterior straight portion extending from said anterior end, followed by a curved portion and ending in a posterior straight portion that extends to said posterior end.

10. The intraocular assembly according to claim 1, wherein said sulcus support portion comprises a suture receiving member and each of said coupling members comprises an anterior end coupled to said sulcus support portion and a posterior end coupled to a perimeter of said posterior intraocular device receiving member, and wherein said anterior end is coupled to said sulcus support portion at said suture receiving member.

11. The intraocular assembly according to claim 1, wherein said at least one anterior restraint member is a continuous 360° member.

12. The intraocular assembly according to claim 1, wherein said sulcus support portion and said anterior blocking members are all along a circumference of said at least one anterior restraint member.

13. The intraocular assembly according to claim 1, wherein said coupling members comprise intraocular device support members.

14. The intraocular assembly according to claim 1, wherein said at least one anterior restraint member comprises a radially-outer circumferential support portion that extends between outer ends of a pair of radial portions, and a radially-inner circumferential support portion that extends between inner ends of each said pair of radial portions.

15. The intraocular assembly according to claim 14, wherein said radially-outer circumferential support portion is circumferentially longer than a circumferential gap between adjacent radially-inner circumferential support portions.

16. The intraocular assembly according to claim 1, further comprising an intraocular device mounted in said sulcus fixation frame, wherein said intraocular device comprises haptics, and wherein said anterior blocking members are configured to block anterior movement of said haptics and a portion of said coupling members is configured to block posterior movement of said haptics.

17. The intraocular assembly according to claim 16, wherein said intraocular device is a cataract IOL.

18. The intraocular assembly according to claim 16, wherein said intraocular device is an Implantable Telescope or IOL.

19. The intraocular assembly according to claim 16, wherein said intraocular device is a toric IOL.

* * * * *